(12) United States Patent
Gould et al.

(10) Patent No.: US 7,507,374 B2
(45) Date of Patent: Mar. 24, 2009

(54) SALIVA SAMPLE TESTING DEVICE

(75) Inventors: Martin Gould, Mullica Hill, NJ (US); Robert Bernstine, Chesapeake City, MD (US)

(73) Assignee: American Bio Medica Corp., Kinderhook, NY (US)

( * ) Notice: Subject to any disclaimer, the term of this patent is extended or adjusted under 35 U.S.C. 154(b) by 710 days.

(21) Appl. No.: 11/252,599

(22) Filed: Oct. 19, 2005

(65) Prior Publication Data
US 2006/0292035 A1    Dec. 28, 2006

Related U.S. Application Data

(63) Continuation-in-part of application No. 11/167,227, filed on Jun. 28, 2005.

(51) Int. Cl.
*G01L 33/497* (2006.01)
*B01L 11/00* (2006.01)
(52) U.S. Cl. .......................................... 422/58; 422/99
(58) Field of Classification Search ................... 422/58, 422/99
See application file for complete search history.

(56) References Cited

U.S. PATENT DOCUMENTS

| | | | | |
|---|---|---|---|---|
| 3,959,141 | A * | 5/1976 | Johnson | 210/132 |
| 4,791,060 | A * | 12/1988 | Chandler | 435/287.2 |
| 4,918,025 | A * | 4/1990 | Grenner | 435/7.94 |
| 4,968,484 | A * | 11/1990 | Nosticzius et al. | 422/68.1 |
| 5,503,985 | A * | 4/1996 | Cathey et al. | 435/7.9 |
| 5,698,406 | A * | 12/1997 | Cathey et al. | 435/7.9 |
| 6,372,182 | B1 * | 4/2002 | Mauro et al. | 422/56 |
| 6,409,909 | B1 * | 6/2002 | Spichiger-Keller et al. | 205/777.5 |
| 7,090,803 | B1 * | 8/2006 | Gould et al. | 422/58 |
| 7,300,632 | B2 * | 11/2007 | Sugiyama et al. | 422/102 |

* cited by examiner

*Primary Examiner*—Jill Warden
*Assistant Examiner*—Rebecca Fritchman
(74) *Attorney, Agent, or Firm*—Edmund M. Jaskiewicz

(57) ABSTRACT

In a lateral test flow immunoassay device, a saliva sample and a buffer solution are delivered into a mixing chamber to mix with a second reagent. The resulting test mixture is allowed to incubate for a pre-determined period of time and then selectively delivered to a test strip.

8 Claims, 19 Drawing Sheets

FIG. 8
FIG. 9
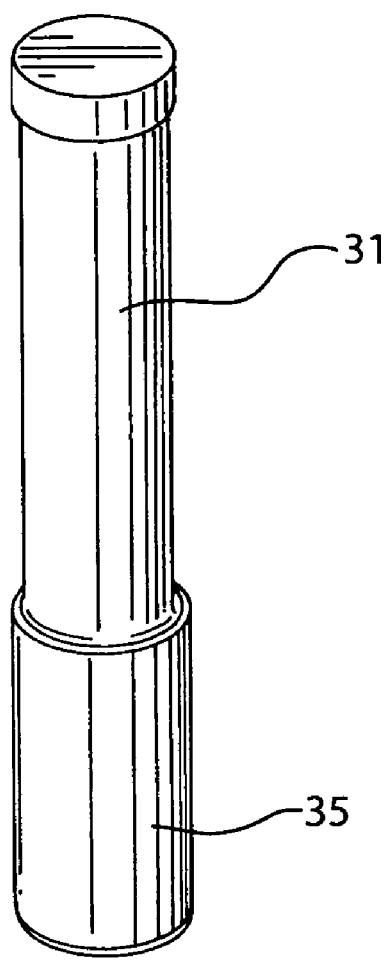
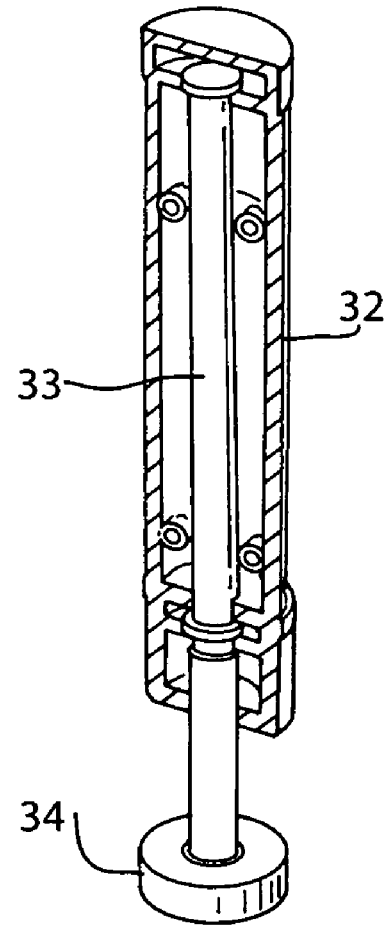

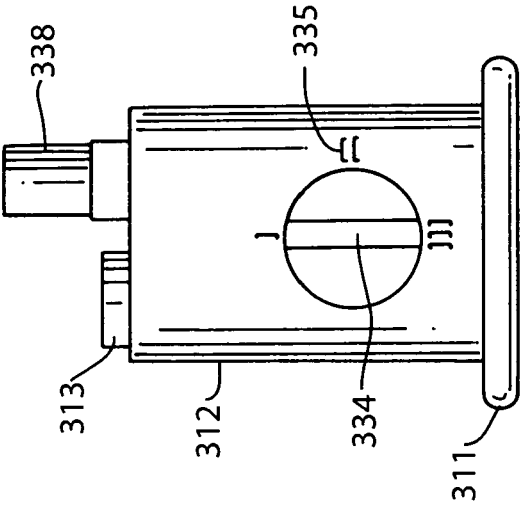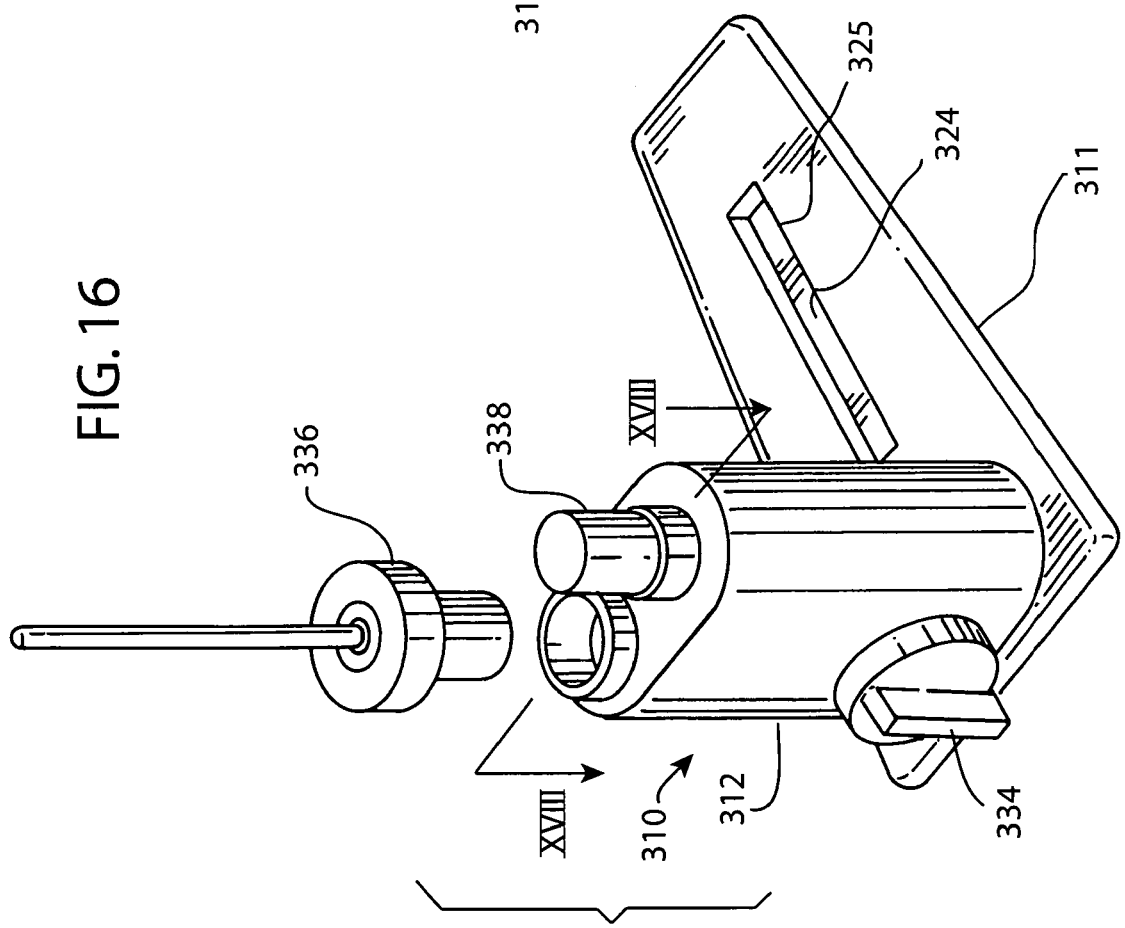

FIG. 22
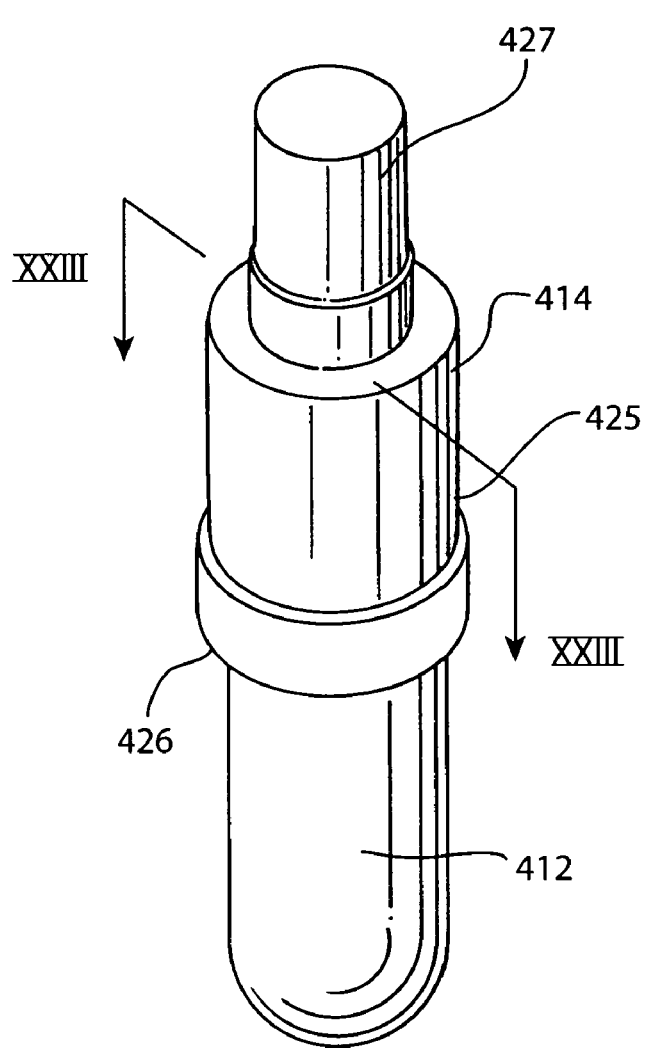
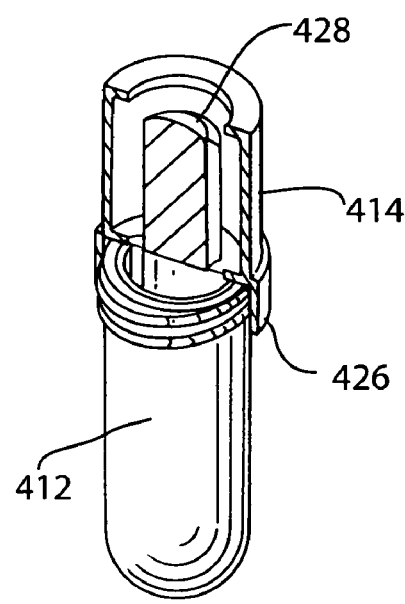
FIG. 23

SALIVA SAMPLE TESTING DEVICE

CROSS REFERENCE TO RELATED APPLICATIONS

The present application is a continuation-in-part of the U.S. patent application Ser. No. 11/167,227 filed Jun. 28, 2005, now pending.

BACKGROUND OF THE INVENTION

1. Field of the Invention

The present invention relates to testing of saliva samples for drugs of abuse, more particularly, to a device and process which permits the saliva sample to be treated and incubated for a predetermined period of time prior to being introduced to an immunoassay test strip.

2. Description of Related Art

The increased availability and use of drugs of abuse by the general population has caused employers, governmental agencies, sports groups and other organizations to utilize drug screening both as a condition of employment and in order to maintain safety in the work place. Screening tests for the detection of drugs of abuse range in complexity from simple immunoassay tests to very complex analytical procedures. Over the years the speed and specificity of immunoassays have made them one of the most accepted methods for screening for drugs of abuse in body fluids. Typical drug screening tests are performed for the purpose of quickly identifying on a qualitative basis the presence of drugs in a body fluid which may be urine or saliva. A complete analysis of the sample may then be carried out in a laboratory only if the preliminary screening results are positive. More and more such drug screenings are taking place on site or at the work place and are generally carried out by testing personnel who are generally not technically trained, such as laboratory technicians. It is thus important that the drug screening procedure is simple but yet reliable. Further, the test apparatus must be such so as to enable the testing personnel to avoid all contact with the fluid specimen which is being tested.

While blood and urine samples have long been the primary fluids used for testing for disease as well as for evidence of substance abuse, there is increasing interest in testing of saliva specimens. Some advantages in testing saliva are that it is relatively easy to obtain a saliva sample and that a saliva sample cannot be adulterated. Also, testing of saliva gives a result in real time within a span of several hours as compared to urine which gives a test result after-the-fact.

However, the collection and analysis of saliva for diagnostic purposes is complicated by the relatively high viscosity of the fluid. Thus, once a saliva test sample is introduced into a test device, there is little user control over the subsequent events since the fluid flow determines the speed and timing of all of the reactions. Also, if the sample requires pre-treatment with specific reagents to dilute or denature interferants, modify analyte structure, or release analyte from binders, such treatments are generally performed outside the confines of the test device. It has become apparent that numerous advantages would be derived from a self-contained saliva sample test device that allows control over the test sample and is simple to use so that more accurate test results may be obtained.

U.S. Pat. No. 6,634,243—Wickstead is such a prior art device which has an inadequate and ineffective provision for control of the test sample. Other relevant prior art includes U.S. Pat. No. 6,267,722—Anderson et al, U.S. Pat. No. 6,214,629—Freitag et al and U.S. Pat. No. 5,630,986—Charlton et al.

U.S. Pat. No. 6,576,193—Cui et al is a prior art device which has a fluid metering valve to control the volume of test fluid released to the test strip, but is not concerned with testing of saliva samples nor with control of speed or timing of reactions involving a saliva test sample.

SUMMARY OF THE INVENTION

It is, therefore, the principal object of the present invention to provide a novel and improved saliva test device and a method of carrying out a saliva test.

It is another object of the present invention to provide such a saliva test device that allows the test sample to be treated and incubated prior to being introduced to the test strip.

It is a further object of the present invention to provide a saliva test device which is simple and easy to operate.

It is an additional object of the present invention to provide such a saliva test device that has selective control over the flow of the test sample to the test strip to increase the sensitivity of the assay, The objects of the present invention are achieved and the disadvantages of the prior art are eliminated by the saliva test device according to the present invention which has a housing having an immunoassay test strip supported therein and a mixing chamber. The housing further has a means for delivering a first reagent to the mixing chamber and a means for delivering a test sample to the mixing chamber in which is formed a first mixture of first reagent and test sample. The housing additionally has a means for delivering a second reagent to the first mixture in the mixing chamber to form a test mixture. There is also a means within the the housing for delivering the test mixture to the test strip after a predetermined period of time has elapsed after the forming of the test mixture.

On one embodiment of the invention this housing may comprise a pair of cylindrical chambers extending vertically and parallel to each other. Each of the chambers has a bottom opening communicating to the mixing chamber. The test strip may be mounted between the cylindrical chamber such that its sample receiving end is adjacent to the mixing chamber. A valve member is interposed between the mixing chamber and the test strip and is movable between open and closed positions. The valve member may comprise a slidable plate having an opening therein and a trigger or operating handle extending to the exterior of the housing for selective operation. The chamber for delivering the first reagent has an upwardly directed piercing member fixed therein which engages a rupturable bottom of a reagent cup container inserted within the chamber. The test sample, preferably on a swab end of a collector, is received within the second chamber when the swab is pushed against an abutment structure such that the sample is expressed from the swab and descends by gravity through a bottom opening to the mixing chamber below.

In a modification of the invention the test strip may be mounted to the side of the second chamber. Further, the slidable plate valve member may be slidable either horizontally or vertically within the housing to open the mixing chamber to the test strip.

The process according to the present invention may comprise providing a testing device having a housing in which is formed a mixing chamber and which supports an immunoassay test strip such that the "results" portion of the test strip is visible from the exterior of the housing. A buffer solution and a test sample are delivered to the mixing chamber to form a first mixture. A binder is delivered to the first mixture to form a test mixture. The test mixture is allowed to incubate for a predetermined period of time and is then delivered to the test strip. The test results are observed on the "results" portion of the test strip.

BRIEF DESCRIPTION OF THE DRAWINGS

Other objects and advantages of the present invention will be apparent upon reference to the accompanying descriptions when taken in conjunction with the following drawings, which are exemplary, wherein:

FIG. 8 is a perspective view of the sample collector shaving a cap to protect the swab;

FIG. 9 is a vertical longitudinal sectional view of the sample collector as shown in FIG. 8.

FIG. 16 is a perspective view of a third modification of the present invention and also showing a sample collector ready to be inserted into the test device;

FIG. 17 is a front elevational view of the test device shown in FIG. 16;

FIG. 22 is a perspective view of the assembled buffer housing and mixing chamber of FIG. 21;

FIG. 23 is a perspective view similar to that of FIG. 22 but showing the buffer housing in a sectional view taken along the line XXIII-XXIII in FIG. 22;

DETAILED DESCRIPTION OF THE INVENTION

Proceeding next to the drawings wherein like reference symbols indicate the same parts throughout the various views a specific embodiment and modifications of the present invention will be described in detail.

Figure 1:
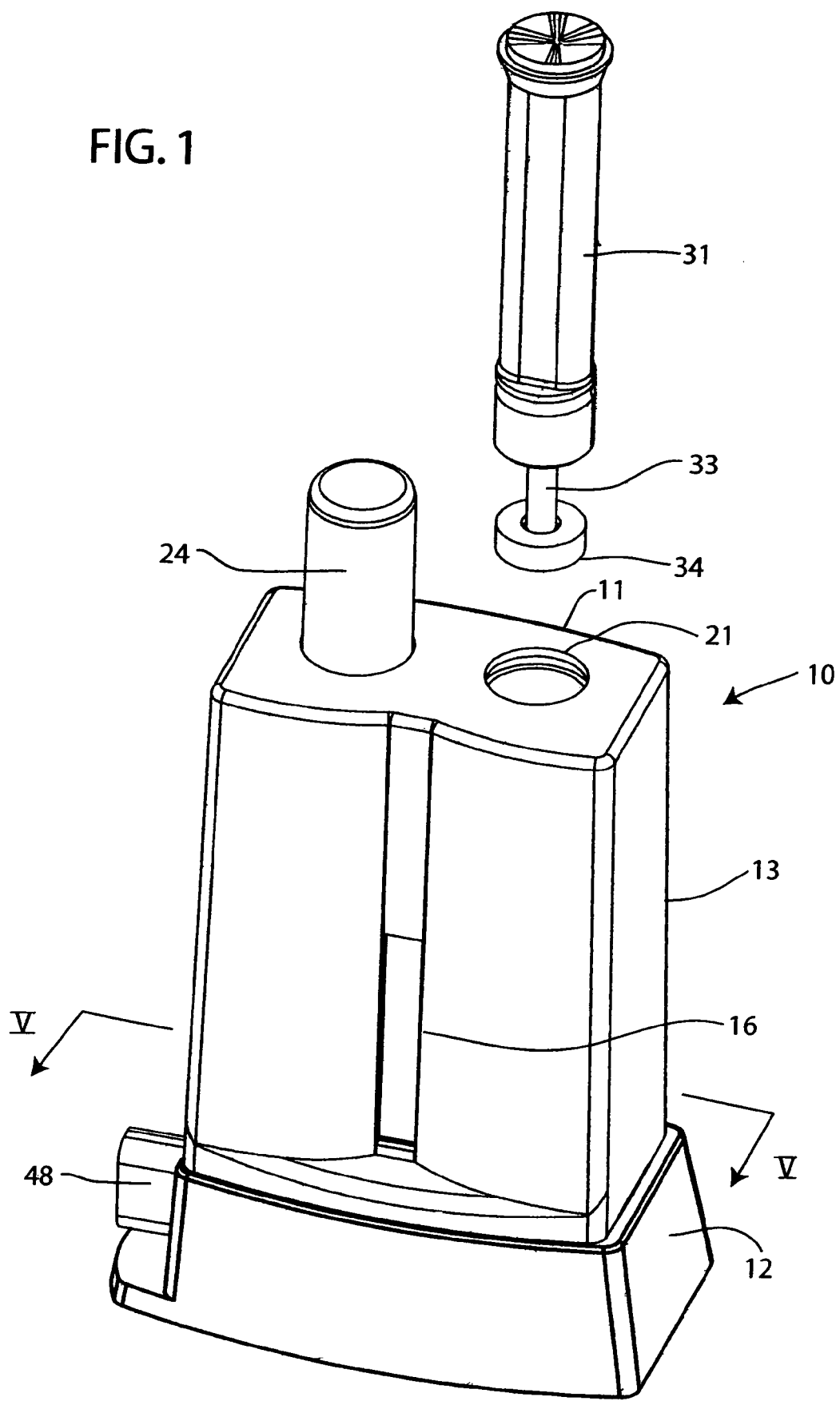
FIG. 1 is a perspective view of the test device according to the present invention and also showing a sample collector in position to be inserted into the device.
Figure 2:
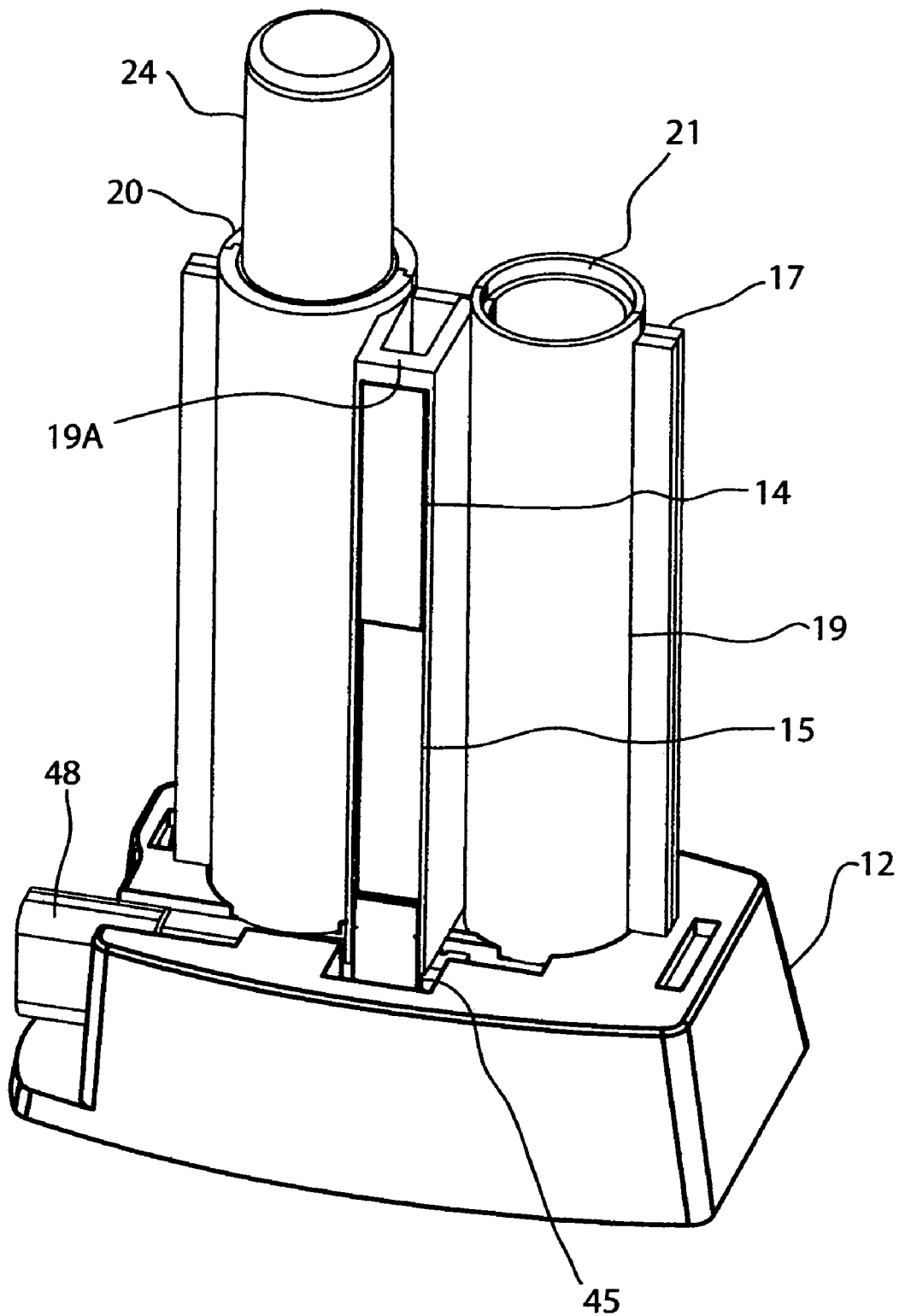
FIG. 2 is a perspective view similar to that of FIG. 1 but showing the housing cover removed.

As may be seen in FIG. 1, a saliva sample testing device according to the present invention is indicated generally at 10 and comprises a body member 11 having a base 12 upon which is mounted a housing 13 within which is supported in a vertical position an immunoassay test strip 14 having a "results" portion 15 which is visible to the exterior through a viewing widow 16 in the housing. The housing 13 also encloses an upper body portion 17 which comprises a rear column structure 18 on to which a front column structure 19 is attached to define a pair of vertical parallel cylinders 20 and 21. The front column 19 has a vertical hollow central portion 19A between the vertical cylinders 20 and 21. Test strip 14 is mounted on the front side of the hollow central portion 19A as seen in FIG. 2.

Figure 3:
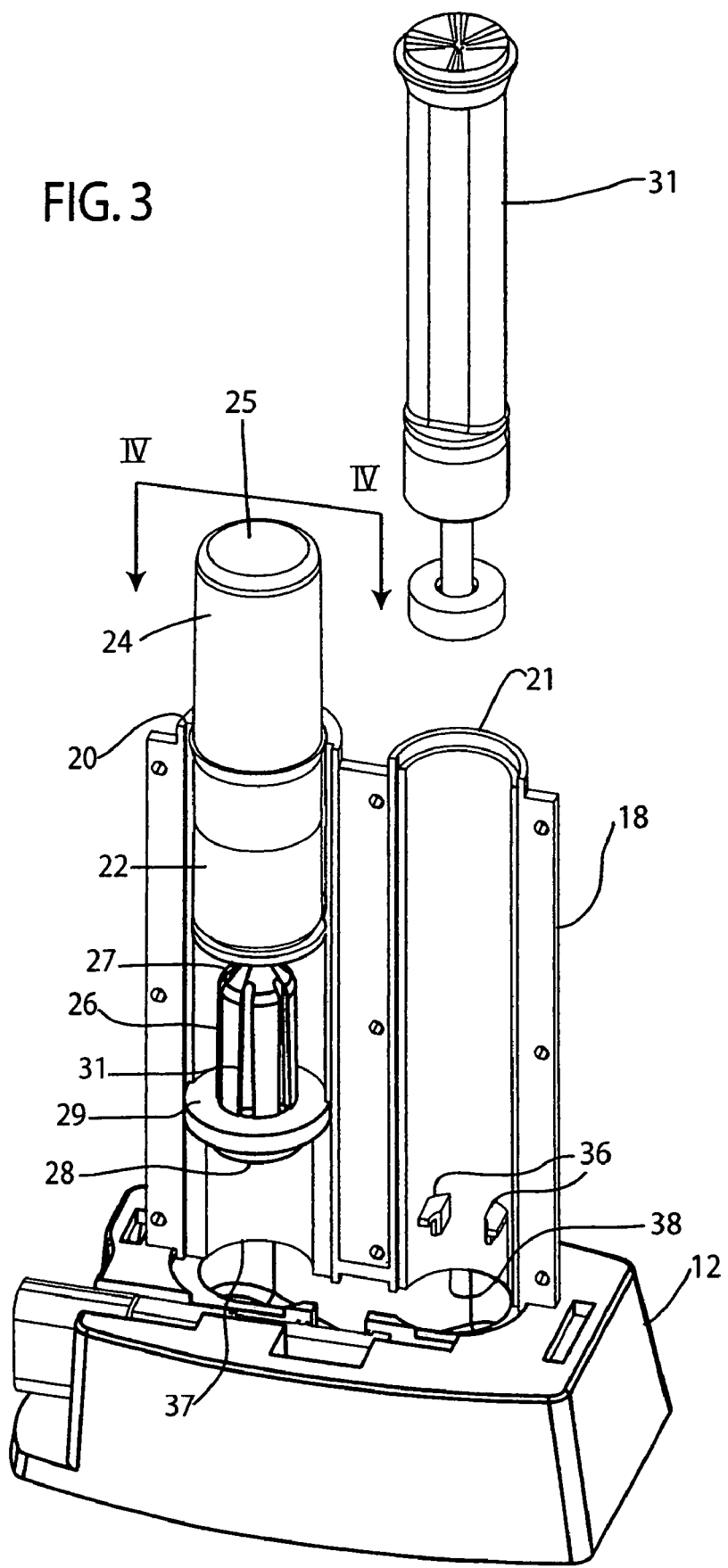
FIG. 3 is a perspective view similar to that of FIGS. 1 and 2 but with the front column removed to show the interiors of the reagents and test cylinders.
Figure 4:
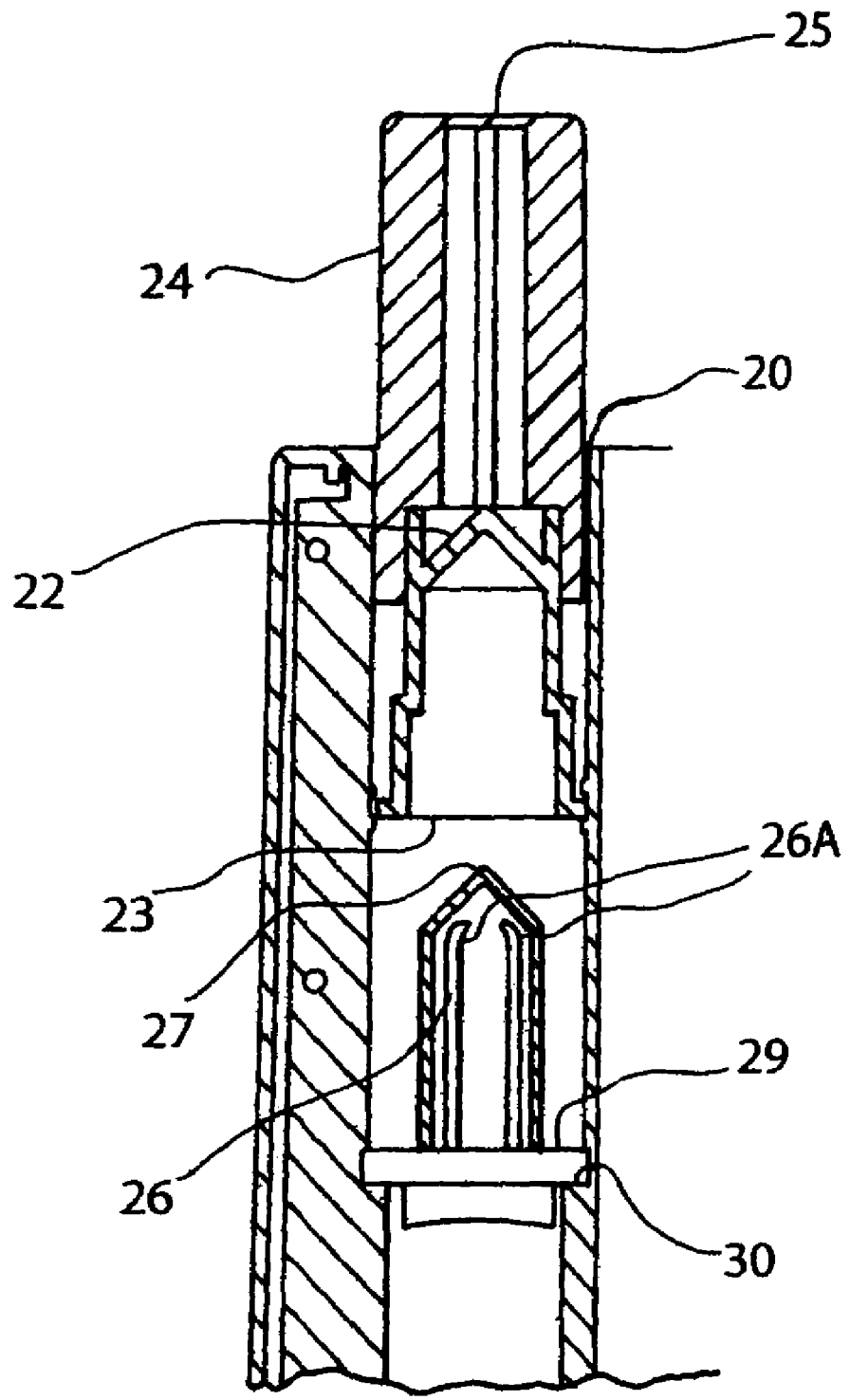
FIG. 4 is a sectional view taken along the line IV-IV in FIG. 3 to show in cross-section the buffer cup and buffer button.

Cylinder 20 delivers a reagent which may be a buffer solution enclosed in a buffer cup 22 and shown in greater detail in FIG. 4. The buffer cup has a bottom 23 formed of a rupturable or pierceable material. A buffer button 24 is positioned on top of the buffer cup such that when a downward force is applied to the top 25 of the buffer bottom, the buffer cup will be forced downwardly and the bottom 23 is ruptured by a piercing member or spike 26 to release the buffer solution within the cup. The piercing member 26, shown in greater detail in FIG. 3, comprises a hollow tubular member having a closed and pointed top end 227 and an open bottom end 28 fixed in an annular member 29 seated and preferably fixed on an annular shoulder 30 on the interior surface of cylinder 20. The piercing member 26 has a plurality of longitudinally extending slots 26A therein to provide paths for buffer solution released from the buffer cup.

The second cylinder 21 receives the sample to be tested and accommodates a sample collecter 31 shown in greater detail in FIGS. 8 and 9. The collector comprises a hollow tubular housing 32 within which is supported a rod 33 the lower end of which extends from the housing and supports thereon an absorbent swab 34 which may be PVA. The swab 34 is enclosed by a removable protective cap 35 which is removed to enable a saliva sample to be collected on the swab 34 and then removed just prior to inserting the collector into the saliva testing device as seen in FIG. 1. Upon absorbing a saliva sample the swab will expand along the rod 33 and may even reach the bottom of the housing 32.

Figure 5:
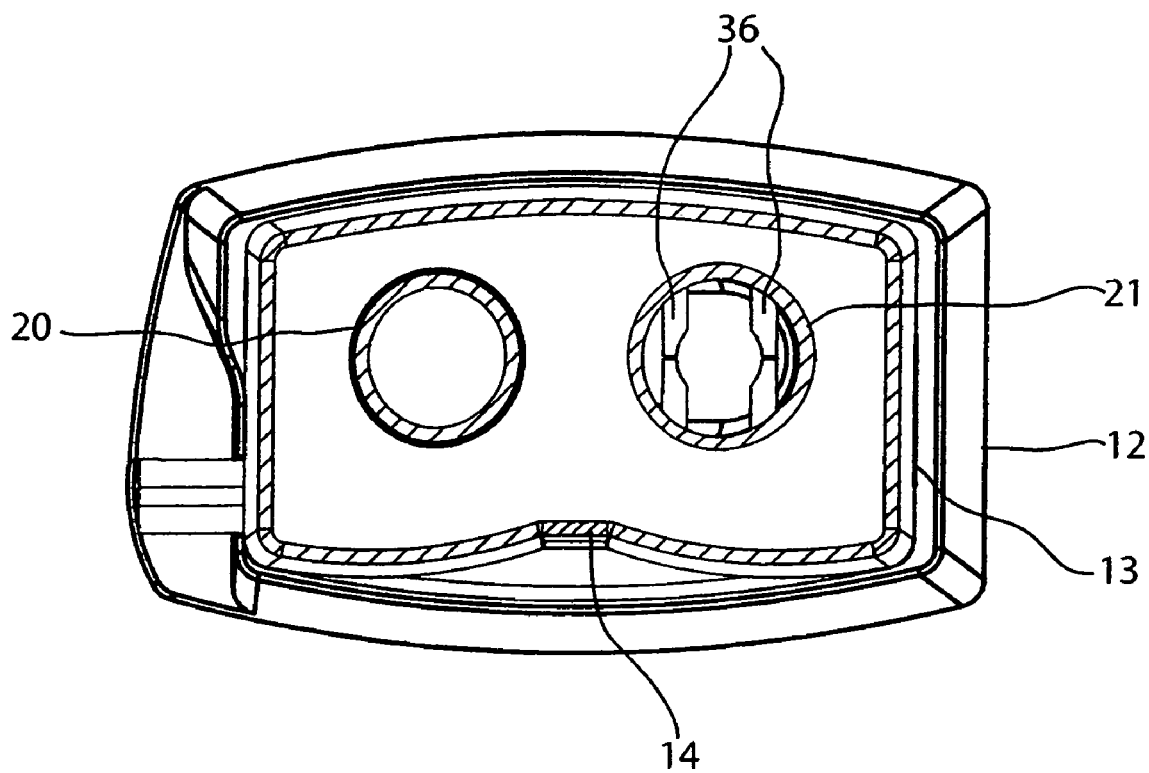
FIG. 5 is a sectional view taken along the line V-V on FIG. 1.

When the collector is inserted into cylinder 21, it is pushed into the cylinder until the swab 34 engages a pair of spaced parallel abutments 36 as may be seen in FIGS. 3 and 5. Continued pressure on the collector will compress the swab 34 against the abutments while the bottom end of the rod passes between the abutments. The saliva sample is thus expressed from the swab and descends downwardly in the cylinder.

Figure 7:
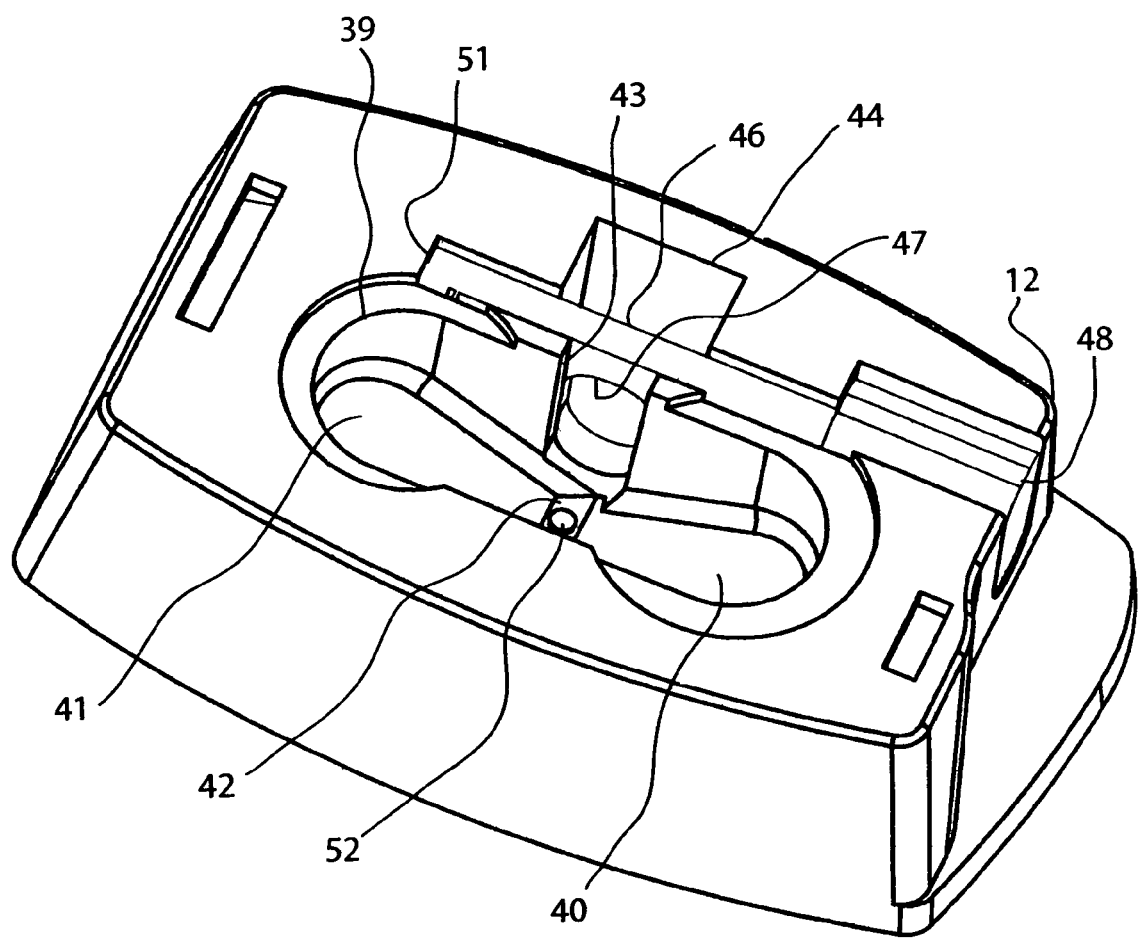
FIG. 7 is a perspective view similar to that of FIG. 6 and showing the mixing chamber and the trigger in the open position.

Cylinders 20 and 21 have bottom openings 37 and 38, respectively, both of which open into a chamber 39 formed within the base 12 and shown in greater detail in FIGS. 7 and 7. The bottom of the chamber 39 is formed by a pair of inclined surfaces 40 and 41 which slope downwardly toward each other to define a mixing chamber 42 at substantially the meeting of the lower edges of the surfaces 40 and 41.

Figure 10:
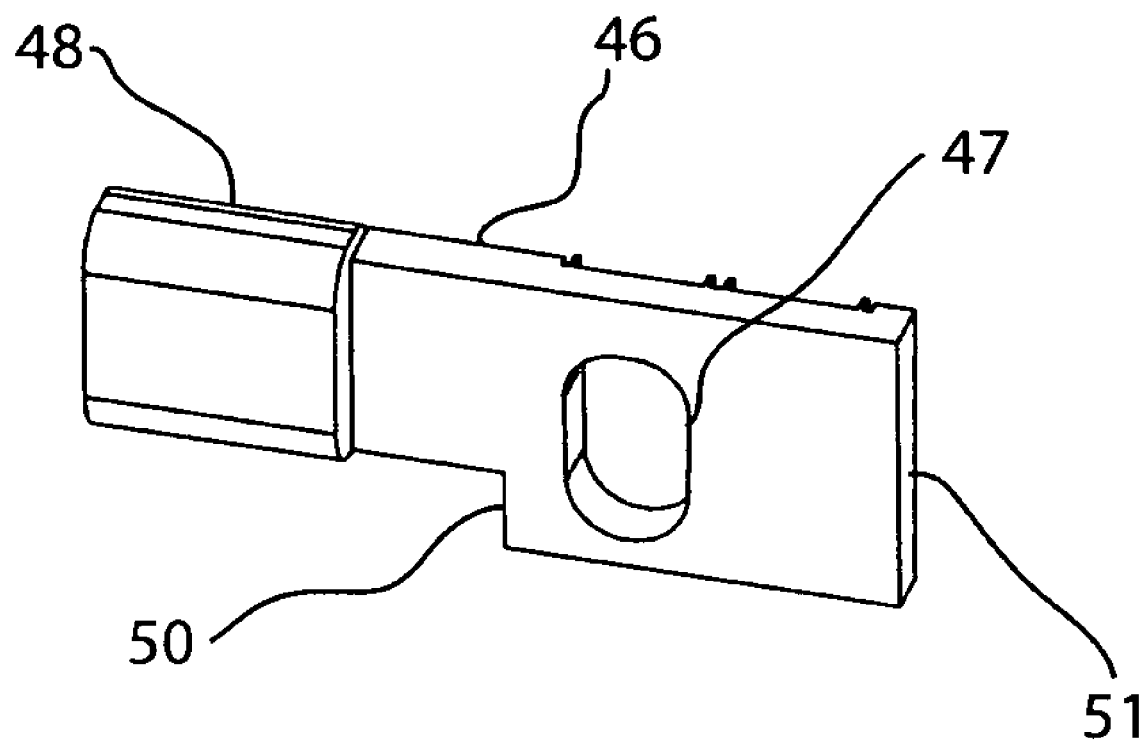
FIG. 10 is a perspective view of the trigger per se which is assembled in the base of the device as seen in FIGS. 6 and 7.

An opening 43 in a side of the base chamber 39 at the location of the mixing chamber 42 communicates with a space or chamber 44 in which is positioned the sample receiving end 45 of the test strip 14. Interposed between the mixing chamber 42 and test strip chamber 44 is a slide valve 46 or trigger shown in greater detail in FIG. 10. The slide valve has an opening 47 therethrough, which when in the position as shown in FIG. 7 provides communication between the mixing chamber 42 and test strip chamber 44. At the end of the valve extending outwardly of the base there is an actuating handle or trigger 48. The valve 46 slides longitudinally within an elongated space 49 configured to limit the movement of the valve in either direction. Movement of the valve 46 to its closed position as seen in FIG. 6 is limited by an abutment 50 on the valve contacting a shoulder within the valve space 49 and movement to its open position is limited by valve end 51 contacting the end of valve space 49 as seen in FIG. 7.

Figure 6:
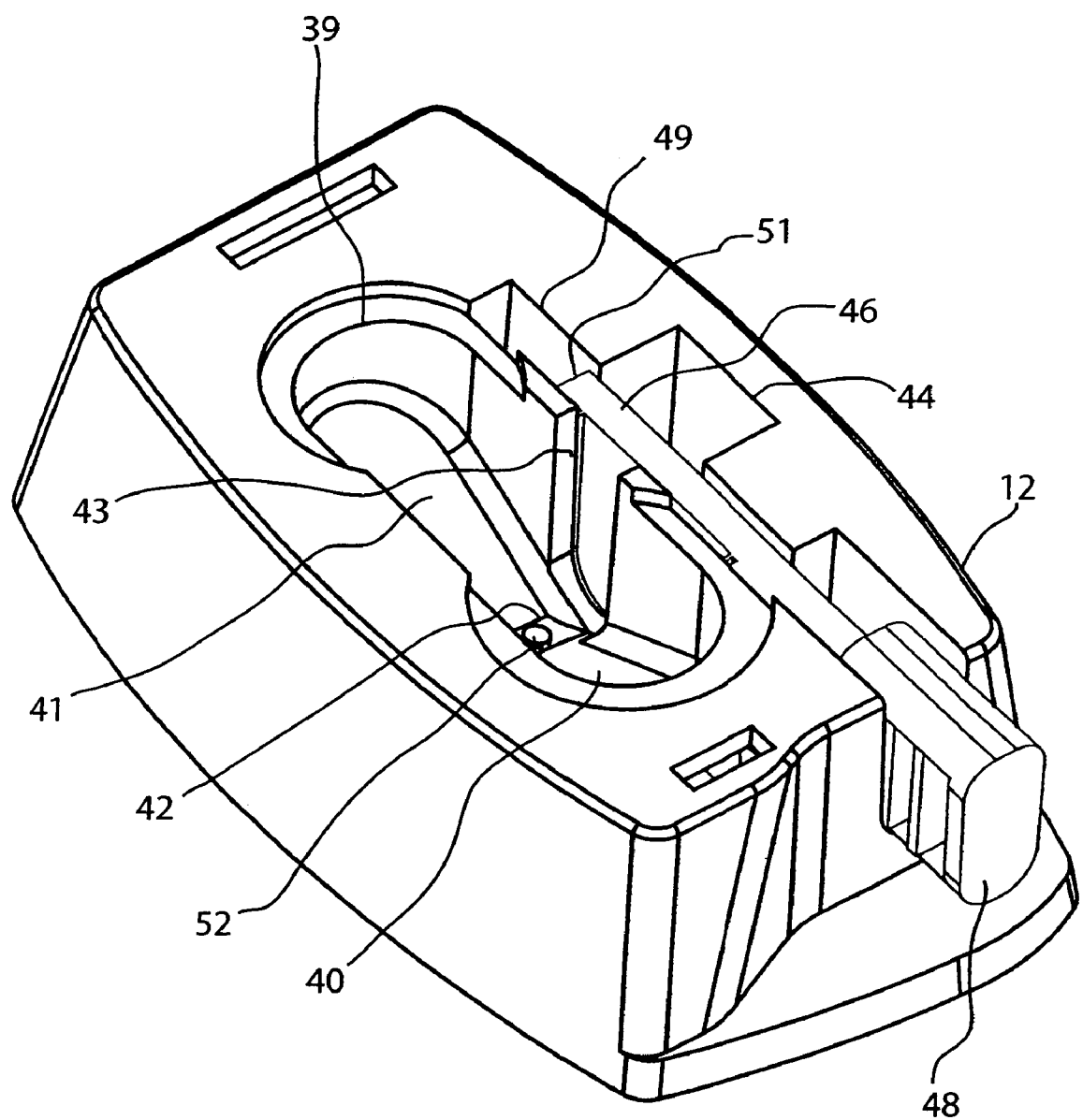
FIG. 6 is a perspective view of the base of the device with the cylinders removed and showing the trigger in the closed position.

A second reagent 52, which may be a binder such as a colloidal gold-antibody complex or an antigen may be stored or positioned during assembly of the testing device in the mixing chamber 42 as shown in FIGS. 6 and 7.

In order to use the device to conduct a test after a saliva sample has been collected on swab 34 of the sample collector 31 the buffer cup button 24 is depressed which urges the bottom 23 of the buffer cup 22 against the piercing member 26 to rupture the bottom 23 and release the buffer solution downwardly onto the bottom sloping surface 40. The buffer solution then flows into, the mixing chamber 42 and reacts with the second reagent 52. The collector cap 35 is removed and the collector swab 34 is inserted into chamber 21 and pushed downwardly to express the saliva sample from the swab as described above. The test sample drops onto the bottom sloping surface 41 to flow downwardly into the mixing chamber 42 to mix with the buffer solution and react with the second reagent 52. Mixing will occur in a matter of 2-3 seconds and the resulting test mixture is allowed to react for a pre-determined period of time. That is, the test mixture is incubated for 2-3 minutes.

After completion of the incubation period, the trigger 48 is pushed inwardly to its open position to provide communication between mixing chamber 42 and test strip chamber 44 to deliver the test mixture to the test strip. Any reactions on the test strip 14 may be observed through the viewing window 16 in the housing.

Figure 11:
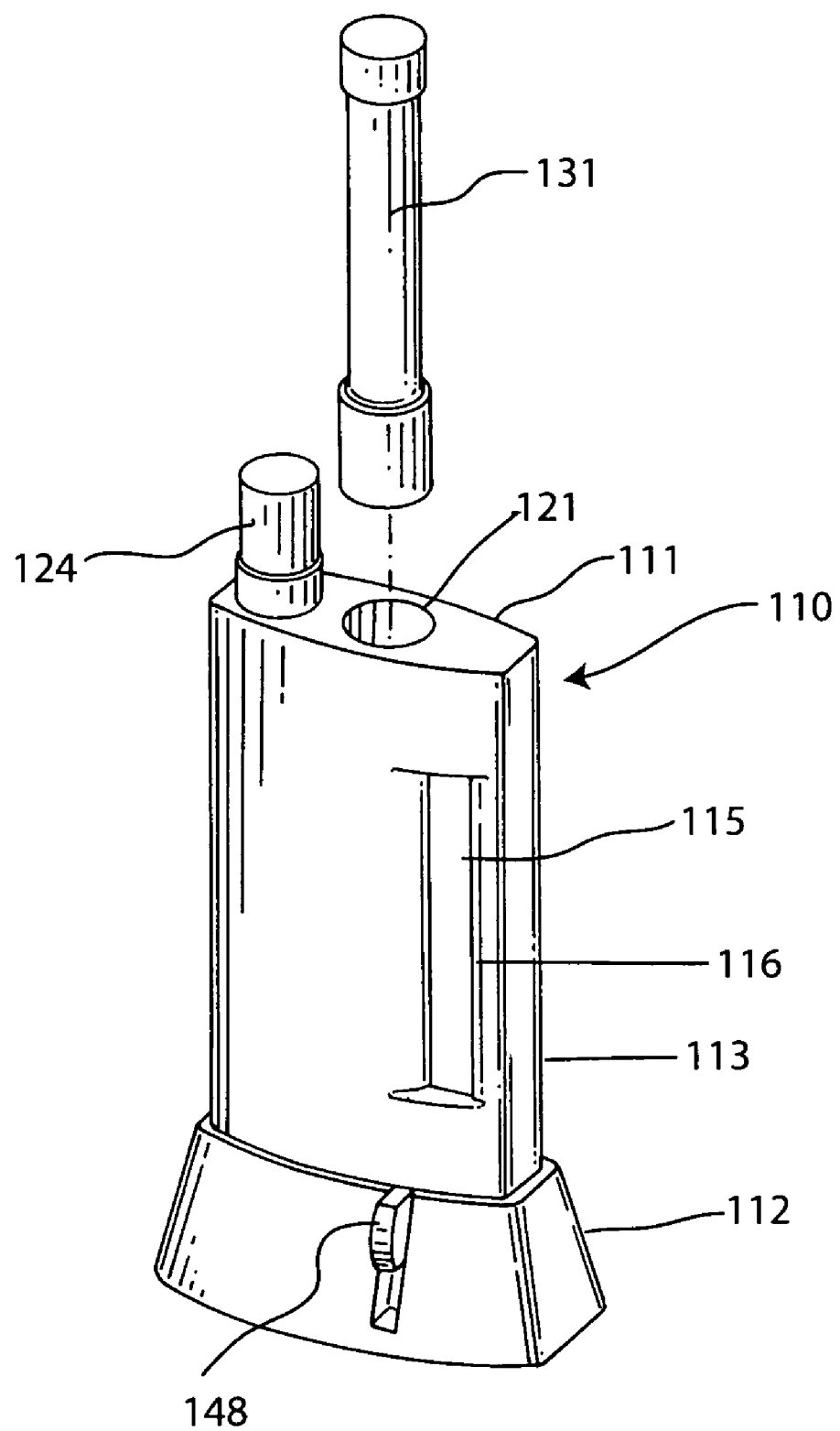
FIG. 11 is a perspective view similar to that of FIG. 1 of a modification of the testing device.
Figure 12:
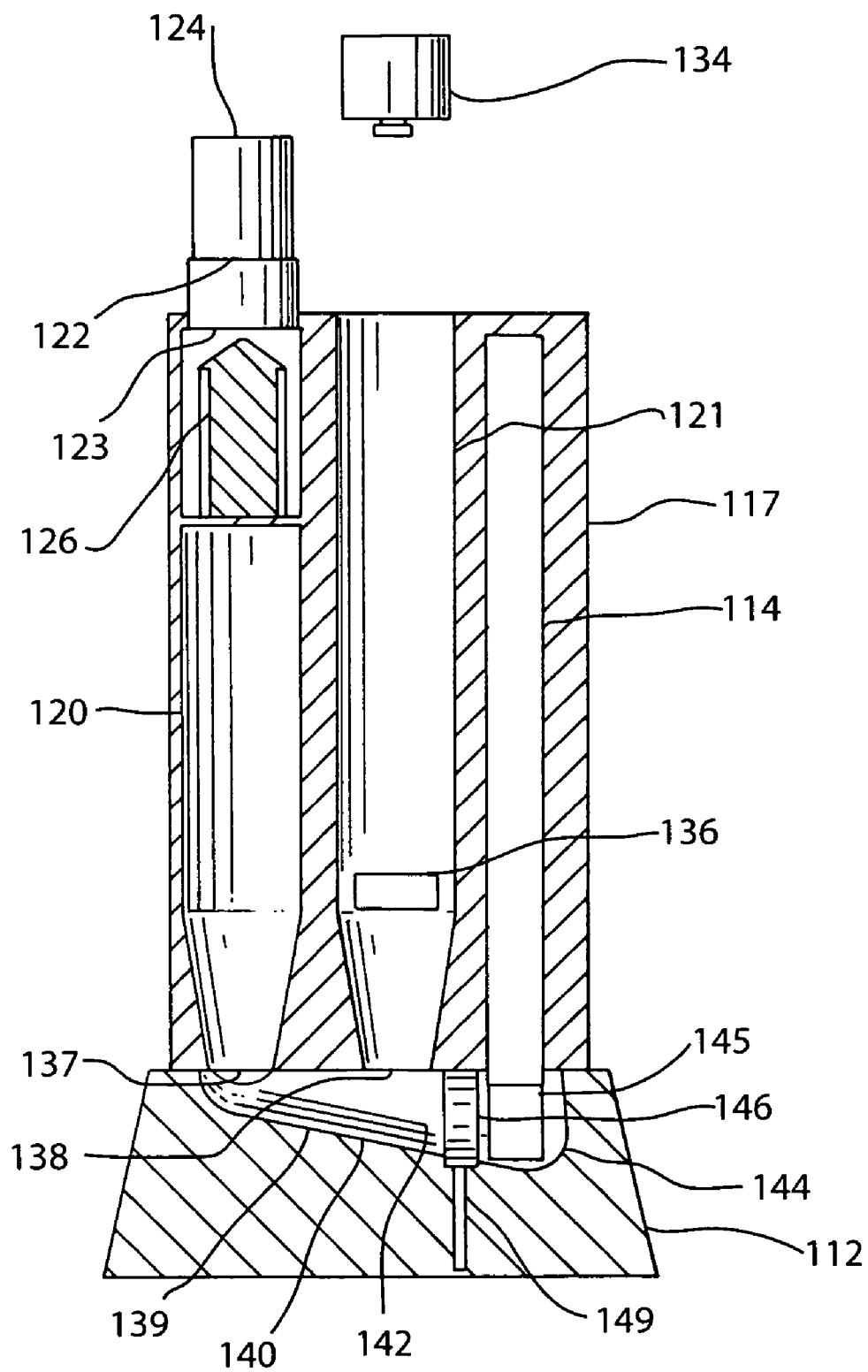
FIG. 12 is a vertical sectional view of the testing device shown in FIG. 11.

In FIGS. 11 and 12 there is shown at 110 a saliva testing device which is a modification of the testing device 10 described above. Testing device 110 similarly comprises a body member 111 having a base 112 upon which is mounted a housing 113 enclosing an upper body portion 117 which has a receiving window 116 therein. A pair of vertical parallel cylinders 120 and 121 are positioned adjacent each other in the upper body portion 117. A test strip 114 is mounted on upper body portion 117 positioned adjacent cylinder 12, and has a results portion 115 visible through window 116. A sample receiving end 145 of the test strip 114 extends into a chamber 144 which communicates with a mixing chamber 142 in the base 112. The cylinders 120 and 121 have bottom openings 137 and 138 opening into a chamber 139 within the base 112 and having an inclined bottom surface 140 which slopes downwardly to the mixing chamber 142. Interposed between the mixing chamber 142 and test strip chamber 144 is a plate slide valve or trigger 146 having an end extending outwardly of the base which has an actuating handle or trigger 148 thereon. In its upper positions as shown in FIGS. 11 and 12, the plate valve 146 closes communication between mixing chamber 142 and test strip chamber 144. The valve plate is slidable vertically and transversely of itself within a valve space 149. The trigger 148 is depressed downwardly to open communication between mixing chamber 142 and test strip chamber 144.

The housing 113 encloses the upper body portion 117 but has the opening 116 which permits viewing of the "results" portion 115 of the test strip 114. The cylinder 120 has on its upper end a buffer button 123 which moves buffer cup 122 downwardly against a piercing member 126. Cylinder 121 receives a sample collector 131 having a sample swab 134 which is pushed against abutments 136 to express a saliva sample downwardly onto the sloping surface 140.

A second reagent may be positioned during assembly of the testing device in the mixing chamber 142.

To operate testing device 110 after a saliva sample has been collected on collector swab 134 of the collector 131, the buffer button 124 is depressed to cause the buffer cup bottom 123 to be pierced by piercing member 126 to release, the buffer solution downwardly onto the sloping surface 140. The collector swab 134 is inserted into sylinder 121 and pushed downwardly to urge the swab 134 against abutments 136 to express the saliva sample downwardly onto the sloping surface 140 to mix with the buffer solution and the resulting mixture mixes with the second reagent in the mixing chamber 142 at the lower end of the sloping surface 140 to form a test mixture. After an incubation period of 2-3 minutes, the trigger 148 is depressed to move the plate slide valve 146 downwardly to open communication between the mixing chamber and test chamber. In the test chamber the test mixture contacts the sample receiving end 145 of the test strip 114. Any reaction on the test strip may be observed through the viewing window 116.

Figure 13:
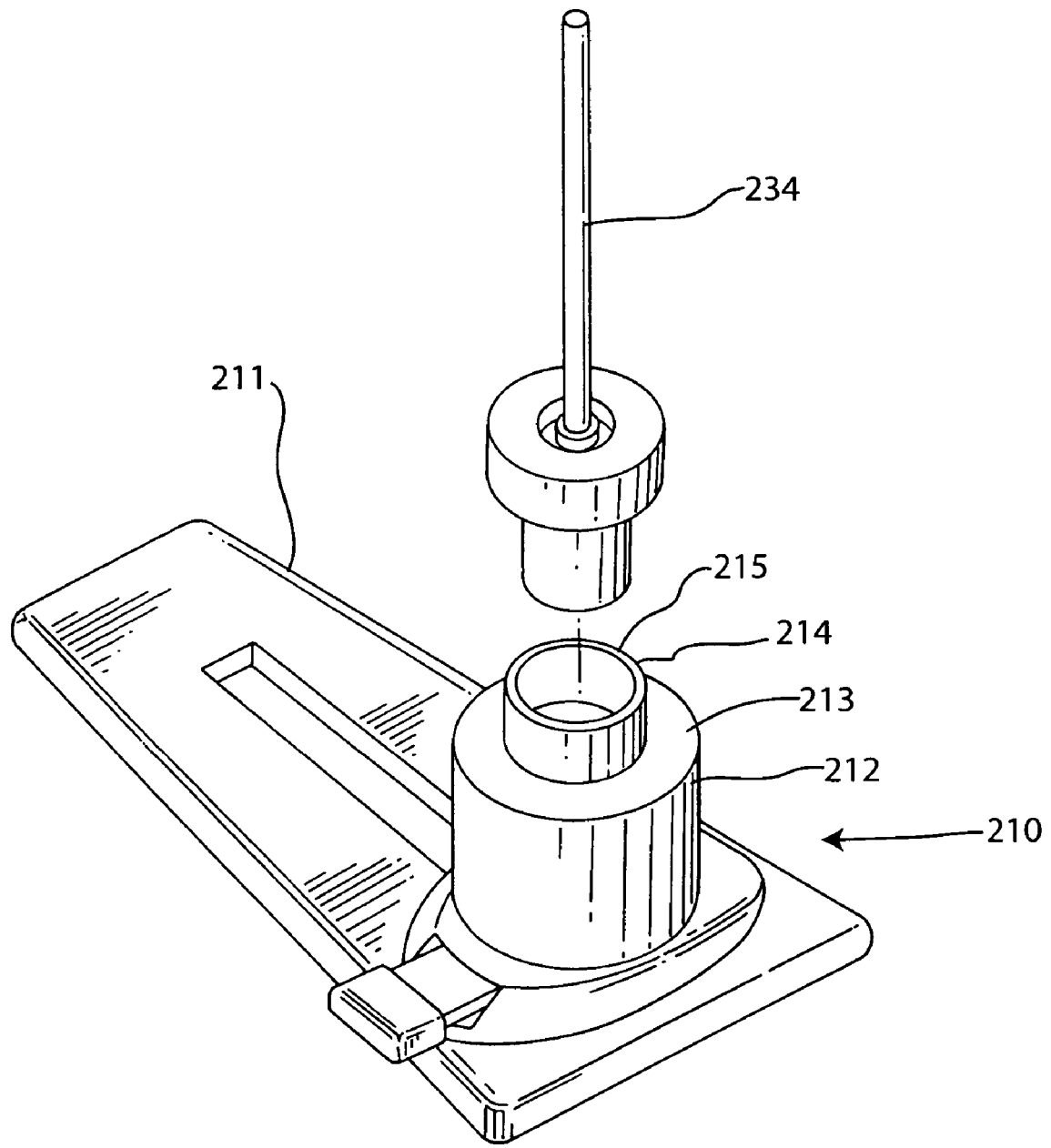
FIG. 13 is a perspective view of another modification of the testing device according to the present inventions.
Figure 14:
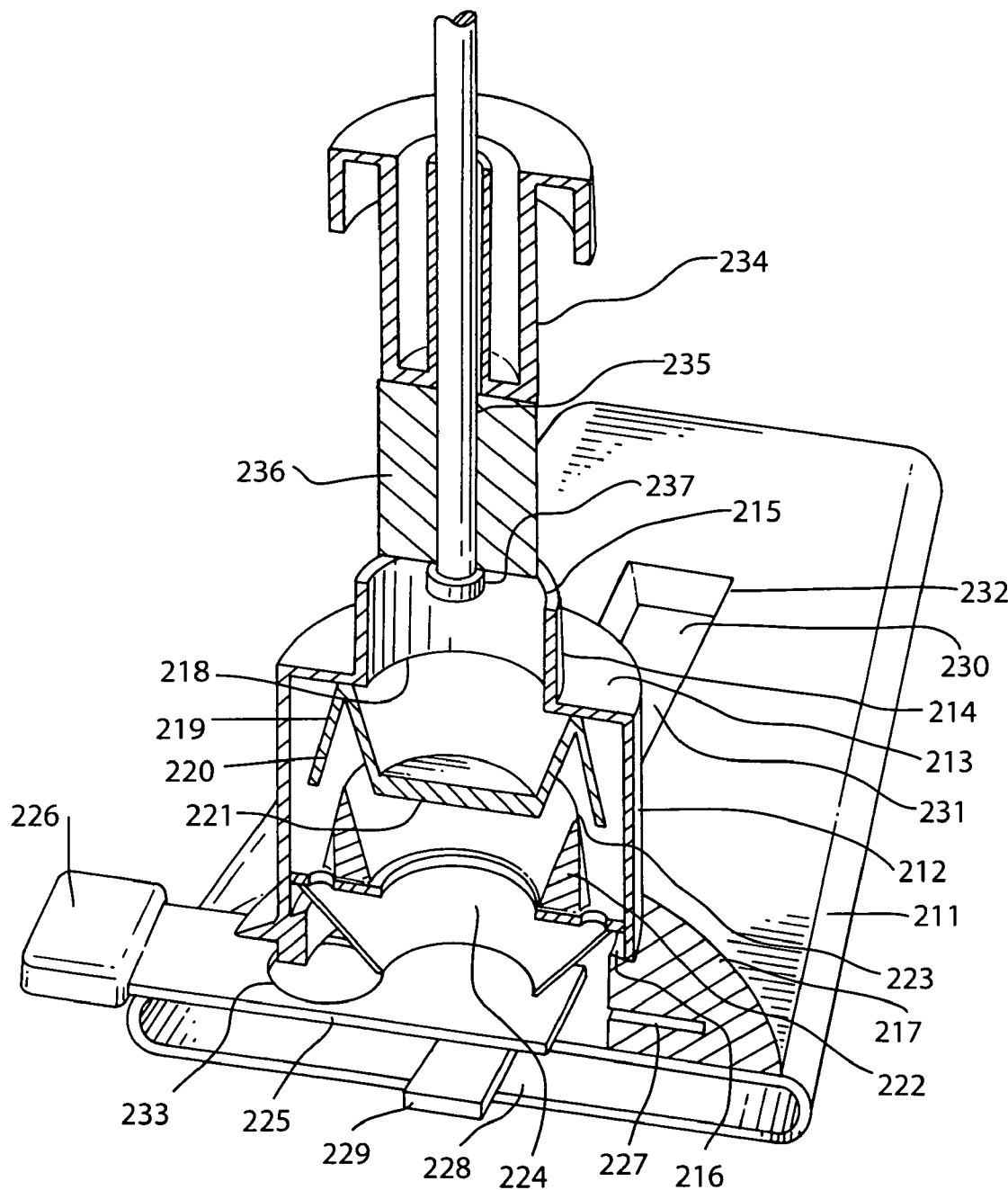
FIG. 14 is a vertical sectional view of the testing device shown in FIG. 13.
Figure 15:
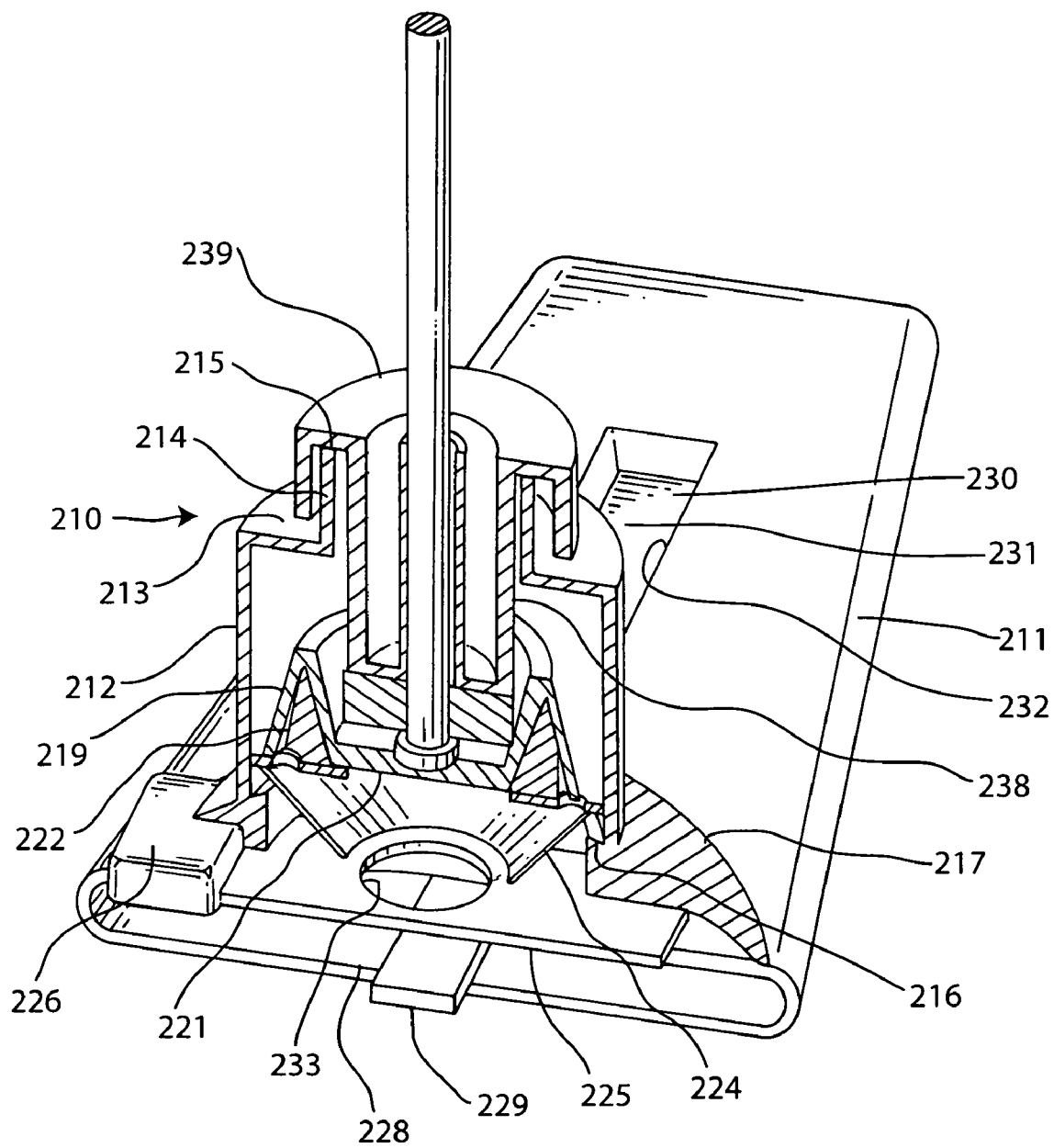
FIG. 15 is a vertical sectional view similar to that of FIG. 13 but showing the trigger depressed to dispense the mixture to the test strip.

In FIGS. 13-15 there is shown at 210 another modification of the testing device of the present invention. Testing device 210 has a flat hollow base 211 upon which is mounted a cylinder 212 having a top 213 upon which is a second but smaller diameter cylinder 214 which has an open top end 215. The cylinders 212 and 214 are aligned vertically and are coaxial with each other The cylinder 212 has a bottom end 216 which opens into a raised position 217 on base 211 which opens to the interior of the base 211 and cylinder 214 has a bottom end 218 which opens into cylinder 212.

Positioned within the cylinder 212 is an annular shaped buffer cup 219 having an inverted V cross-section, as shown in FIG. 14, and having a bottom 220 closed by a rupturable material. A cross-piece 221 extends diametrically across the buffer cup 219. Mounted below the buffer cup 219 is an annular spike or piercing member 222 having a cross-section conforming to the cross-section of the buffer cup 219 and a sharpened top edge 223 engageable with the bottom 220 of buffer cup 219. Below the spike 222 is a frusto-conical shaped mixing chamber 224 tapering inwardly in a downward direction and closed off by a plate slide valve 225 having a trigger 226. The valve 225 is slidable longitudinally within a valve chamber 227 formed within the base raised portion 217. Below the mixing chamber 224 is a test chamber 228 within which is positioned the sample receiving end 229 of a test strip 230. Test strip 230 has a results portion 231 which is visible through a viewing window 232 formed in the top wall of the base 211.

The slide valve 225, as shown in FIG. 14, in its closed position, has an opening 233 therein which opens the bottom of the mixing chamber 224 to the test chamber 228 as shown in FIG. 15 when the trigger 226 is depressed or pushed inwardly of the testing device.

The top end 215 of cylinder 214 receives a sample collector 234 which has a central rod 235 on the lower end of which is mounted a sample collector swab 236. The rod 235 has a flattened and enlarged end 237 which is engageable with the crosspiece 221 in buffer cup 219 and also retains the swab 236 on the rod. Also mounted on the rod 235 and above the swab 236 is a cylindrical plunger 238 which bears against the upper surface of swab 236 and has an annular flange 239 which engages the top edge of open end 215 of cylinder 214.

A second suitable reagent is positioned in the mixing chamber during assembly of the testing device.

In operation of the testing device 210 after a saliva sample has been collected on the swab 236, the collector is introduced into into the top end 215 of cylinder 214 as shown in FIG. 14. The collector central rod 235 is pushed downwardly to engage the rod end 237 with buffer cup crosspiece 221. Continued downwardly pushing of rod 235 will cause the bottom of buffer cup 219 to be ruptured by spike top edge 223 to release buffer solution into the mixing chamber 224. The annular flange 239 is pushed downwardly to squeeze the swab and to express saliva sample therefrom into the mixing chamber to mix with the buffer solution and with a second reagent in the mixing chamber to form a test mixture. After an incubation period of 2-3 minutes, the trigger 226 is pushed inwardly to deliver the test mixture through valve opening 233 into the test chamber 228 and sample receiving end 229 of the test strip. Any reactions on the test strip may be viewed through window 232.

Figures 18, 19:
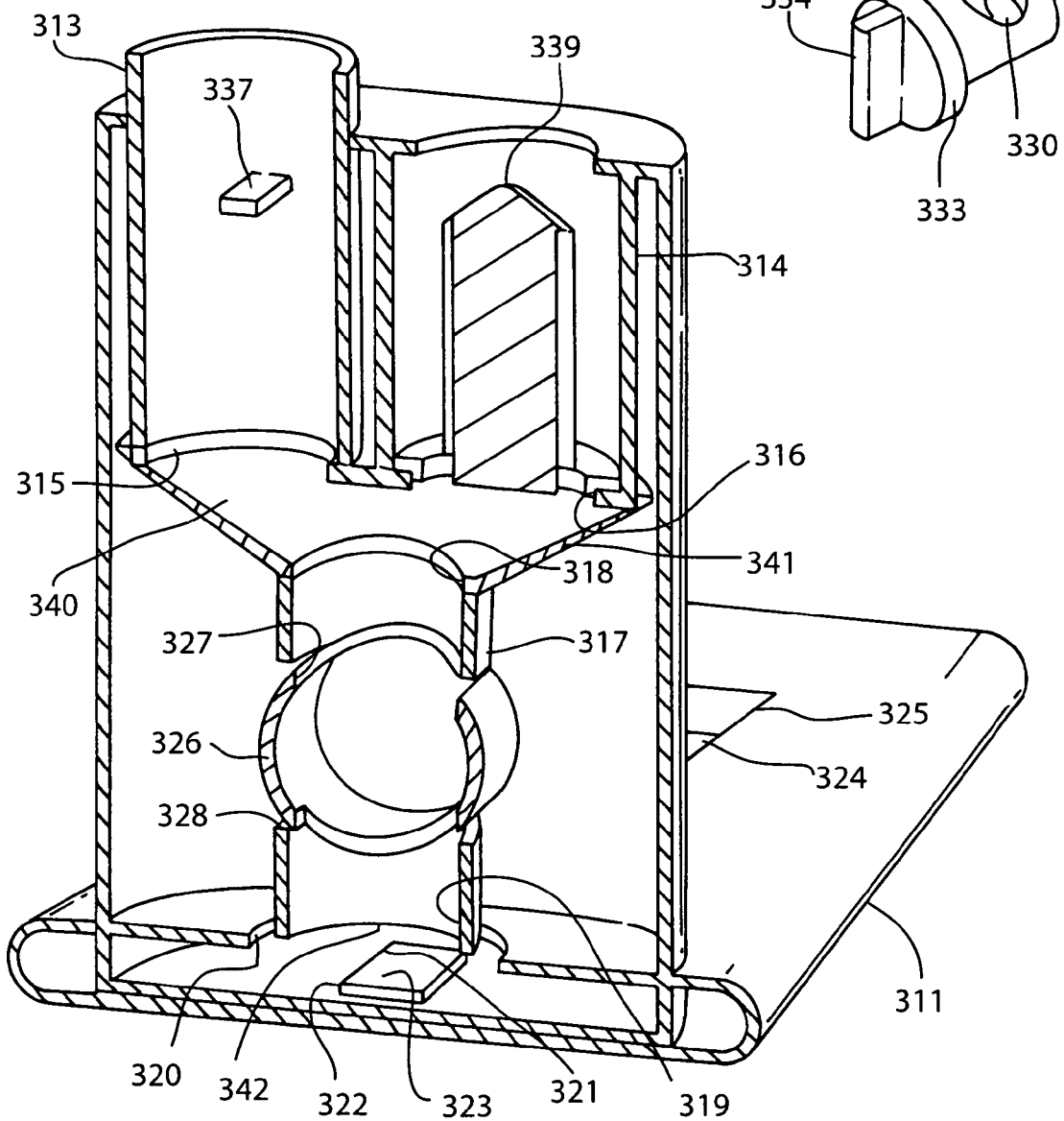
FIG. 18 is a vertical sectional view taken along the line XVIII-XVIII in FIG. 16.
FIG. 19 is a perspective view of the control cylinder removed from the test device in FIG. 16.

In FIGS. 16-20 there is shown at 310 a further modification of the present invention. Testing device 310 has a flat hollow base 311 upon which is mounted a body member 312 within which is a cylindrical chamber 313 and a second cylindrical chamber 314 as seen in FIG. 18. The chambers 313 and 314 are mounted vertically in parallel side-by-side relationship and the chambers have bottom openings 315 and 316 respectively. Below the cylindrical chambers 313 and 314 is a vertical passage 317 having a top end opening 318 and a bottom end opening 319 which communicates through an opening 320 in the top wall of base 311 into a test chamber 321 within the base 311. An immunoassay test strip 322 is disposed horizontally within the test chamber and has a sample receiving end 323 under opening 320 and a results portion 324 exposed through a viewing window 325 formed in the top wall of base 311.

A cylindrical tubular member 326 passes transversely through the vertical passage 317 intermediate the ends thereof. The tubular member 326 has a pair of opposed openings 327 and 320 which are aligned with and open to the vertical passage 317.

Figure 20:
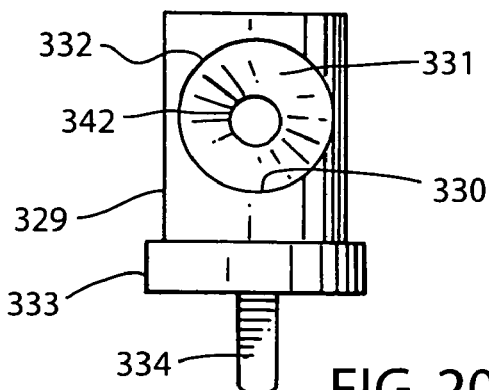
FIG. 20 is a top plan view of the control cylinder shown in FIG. 19.
Figure 21:
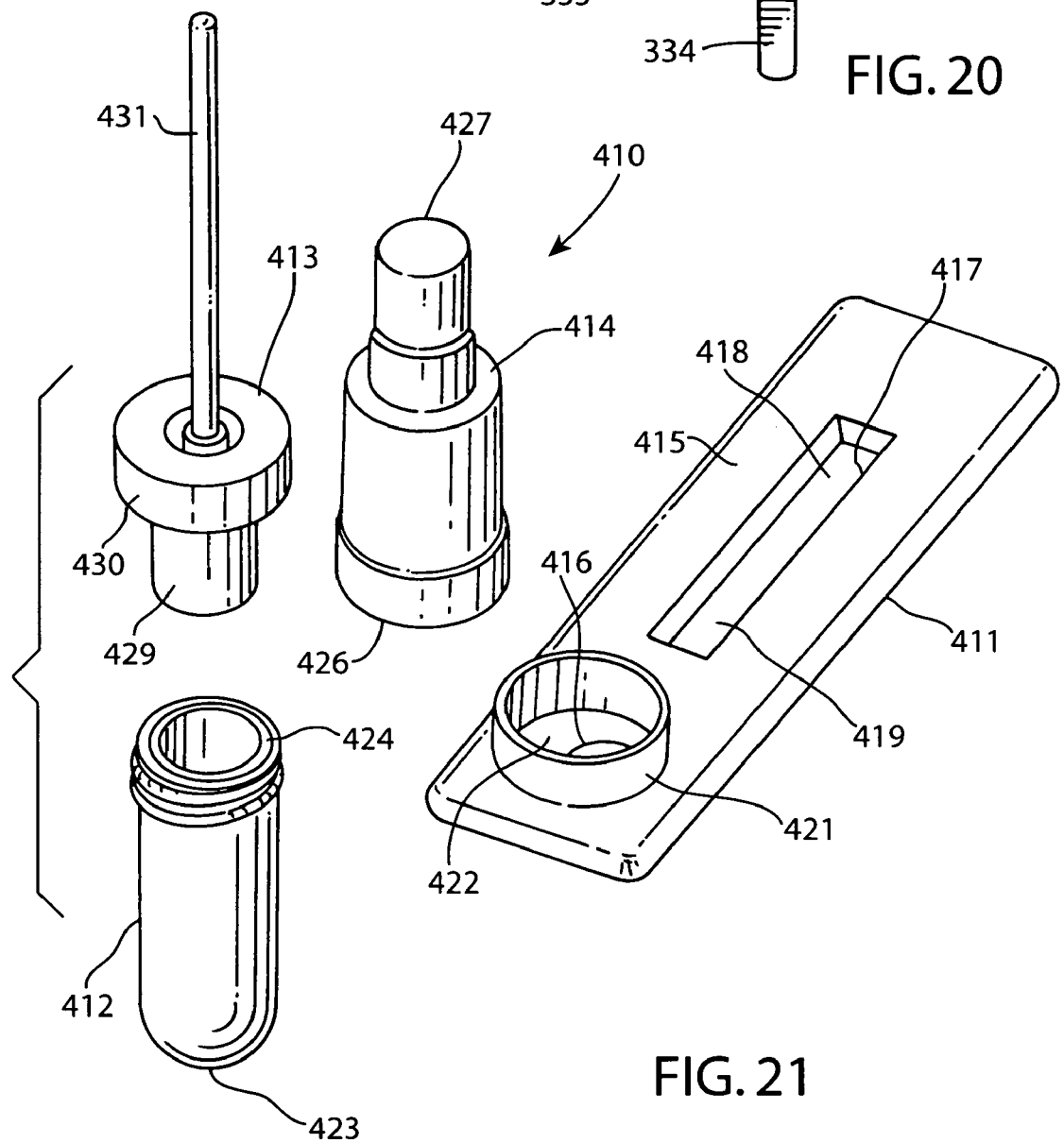
FIG. 21 is an exploded view in perspective of the components of a fourth modification of the present invention.
Figure 25:
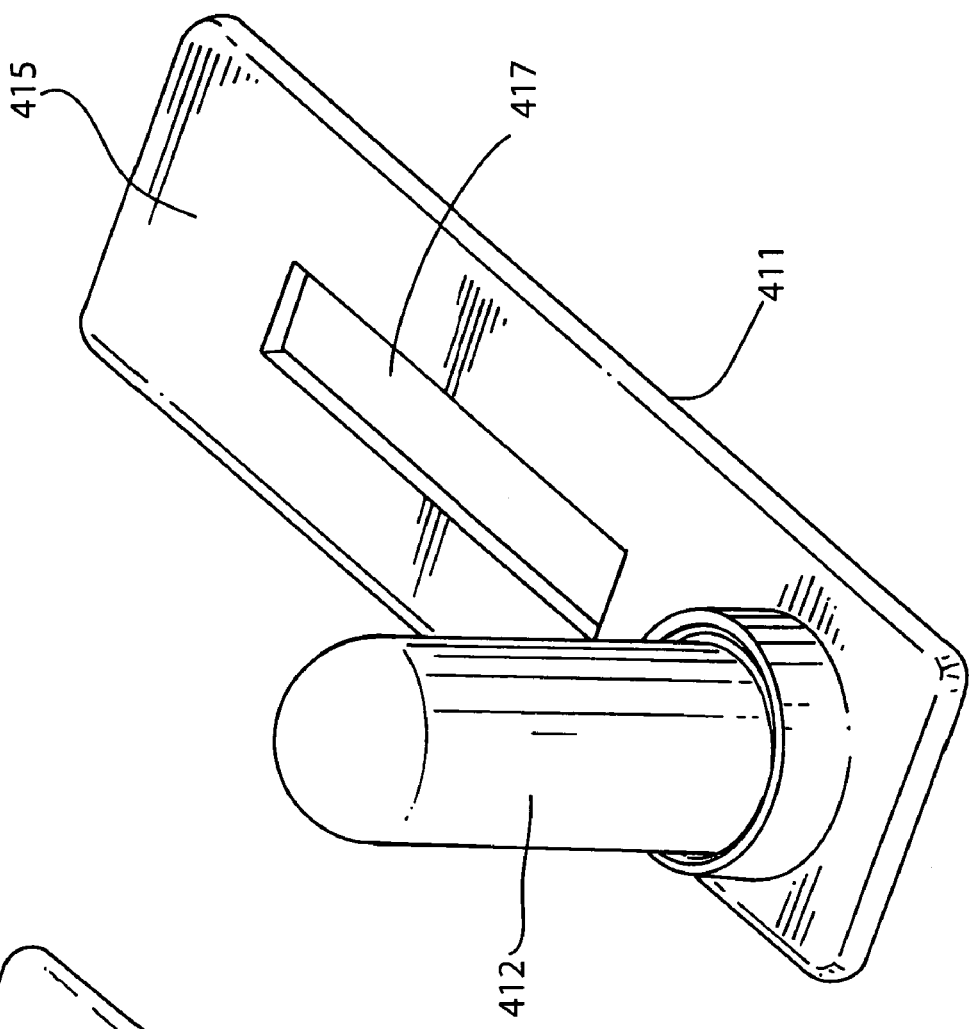
FIG. 25 is a perspective view of the attached body member and mixing chamber in FIG. 24 but in an inverted position to run the test.

Rotatably mounted within the tubular member 326 is a control cylinder 329 shown in FIGS. 19 and 20. The control cylinder 329 has a hollow mixing chamber 330 having a bottom 331 therein and a top opening 332 diametrically opposed from the bottom. One end of the control cylinder 329 protrudes outwardly of the front wall of the body member 312 and has a circular flange 333 on the outerface of which is mounted a raised diametrically disposed handle 334.

Also on the body member front wall advacent the periphery of the control flange 333 are indicia 335 which indicate the positions of the mixing chamber. There is further a "snap" feedback at each indicated position. In position "1", the mixing chamber opening is directed upwardly toward the bottom end openings of the cylindrical chambers and the bottom is directed downwardly toward test chamber 321.

The cylindrical chamber 313 receives the sample to be tested and accommodates a sample collector 336 which may be similar to and functions in the same manner as sample collector 31 shown in FIGS. 8 and 9 and described above. The cylindrical chamber 313 is also provided with an abutment structure 337 which may be similar in structure and functions to the parallel abutments 36 described above and shown in FIGS. 3 and 5.

The cylindrical chamber 314 receives a reagent which may be a buffer solution enclosed in a buffer cup 338 similar in structure and function to the buffer cup 22 shown and described above. Chamber 314 is also provided with a piercing member 339 similar in structure and function to piercing member 26 in chamber 20 shown and described above.

Below the chamber bottom openings 315 and 316 are inclined surfaces 340 and 341, respectively which slope downwardly and inwardly to connect with the top end opening 318 of vertical passage 317 as seen in FIG. 18.

A second reagent 342, which is preferably a binder such as a colloidal gold-antibody complex or an antigen may be stored or positioned on the bottom 331 of the mixing chamber 330 during assembly of the testing device. The reagent 342 may be in the form of a dry dot or pellet similar to 52 shown in FIGS. 6 and 7 above.

In order to conduct a test with the device 310 after a saliva sample has been collected on the swab of the sample collector 336 in a manner similar to that of the sample collector 31 described above, the buffer cup 338 is depressed. This movement urges the bottom of the buffer cup 338 against the piercing member 339 to rupture the buffer cup bottom which then releases the buffer solution downwardly onto the sloping surface 341. The buffer solution then flows into the mixing chamber 336 and reacts with the second reagent 342. The control cylinder 329 is pivoted to position "2" (see FIG. 17) to cause a thorough mixing of the buffer solution and the second reagent.

The control cylinder is then returned to position "1" and the test sample is dispersed into the mixing chamber 330, as described above into the solution of buffer and second reagent. The collector shaft may then be removed from the collector 336.

The control cylinder is again turned to position "2" to mix the test sample with the solution of buffer and second reagent and to incubate this test mixture for about 3 minutes.

The control cylinder is then turned to position "3" to deliver the test mixture through opening 320 onto the sample receiving end 323 of the test strip 322.

The results of the test will be visible on the test results portion 324 of the test strip after about 3 minutes and can be viewed through the viewing window 325.

In FIGS. 21-25 there is shown at 410 the disassembled components of another modification of the testing device of the present invention. This modification comprises a body member 411, a mixing chamber 412, a sample collector 413 and a buffer cap 414.

The body member 411 is similar to the base 311 described above and comprises a flat hollow portion having a top surface 415 in which is formed a circular opening 416 and a receiving window 417 through which the test results portion 418 of a test strip 419 is visible. The test strip has a sample receiving end 420 which is positioned under the circular opening 416. The opening 416 is enclosed by a circular vertical flange 421 and there is an inclined conical surface 422 at the bottom of flange 421 sloping toward the opening 416.

The mixing chamber 412 is a cylindrical tubular members having a rounded closed end 423 and an open end 424. A second reagent such as 342 described above is positioned on the inner surface of closed end 423 of the mixing chamber 412 but is not shown in the drawings.

The buffer cap 414 is initially assembled detachably mounted on the mixing chamber as shown in FIGS. 22 and 23 and comprises a cylindrical housing 425 having an open end 426 which fits snugly upon the mixing chamber open end 424. The inter-engaging ends of the mixing chamber and buffer cap may be threaded or provided with annular ribs to result in a close snug fit.

Mounted in the top end of the buffer cap is a buffer cup 427 having a rupturable bottom similar to that described above in buffer cup 22. A piercing member 428 is mounted within the buffer cap similar to that described above.

The test sample collector 413 is similar to collector 335 described above and has a swab 429 which absorbs the test sample of saliva. Collector 413 has an annular cap 430 within which is mounted a central rod 431.

In order to conduct a test using the test device 410, the buffer cup 427 is depressed manually to urge the bottom of the buffer cup 427 against the piercing member 428 to rupture the bottom of the buffer cup and release the buffer solution downwardly into the attached mixing chamber 412 as shown in FIGS. 22 and 23. The buffer solution then mixes with the second reagent which has been pre-positioned in the bottom of the mixing chamber.

The buffer cap 414 is then removed from the top of the mixing chamber and the collector cap 430 is attached to the top end 424 of the mixing chamber. The test sample is then expressed from the swab 429 by a suitable structure as described above, to mix with the buffer and second reagent mixture in the mixing chamber to form a test mixture.

Figure 24:
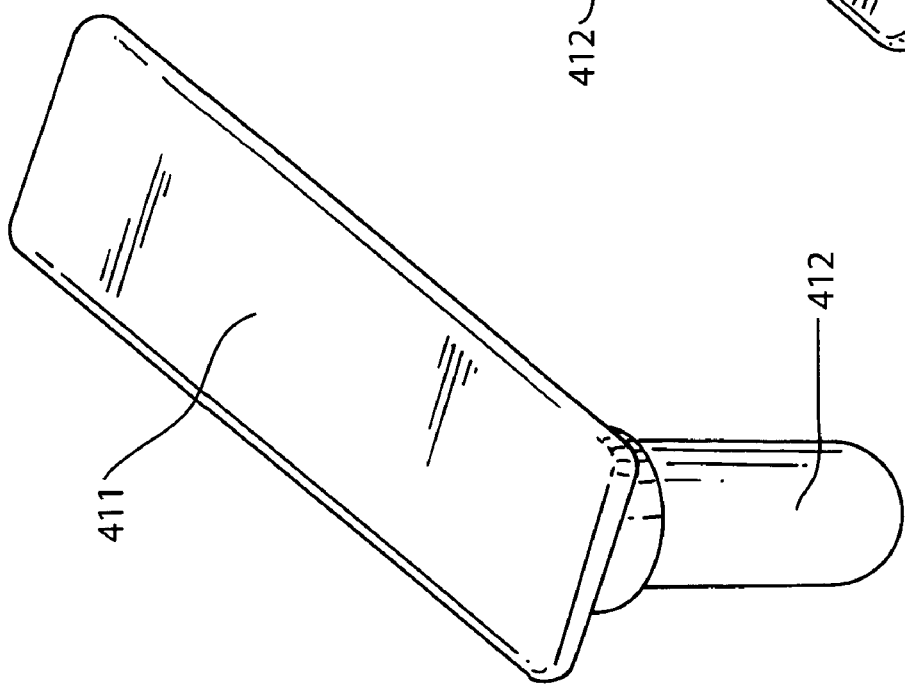
FIG. 24 is a perspective view showing the body member attached to the mixing chamber of FIG. 21.

The collector is next removed from the mixing chamber open end 429 and the body member 411 is attached to the mixing chamber by mounting the flange 421 onto the top end 424 of the mixing chamber held in a vertical position as shown in FIG. 24. The assembled mixing chamber and body member is then inverted or flipped over into the position shown in FIG. 25. This enables the test mixture within the mixing chamber to flow downwardly by gravity onto the sample receiving end 420 of the test strip. This begins the test and the test results can then be viewed in about 3 minutes through viewing window 417 in the top surface 415 of the body member 411.

Thus it can be seen that the present invention discloses a lateral flow immunoassay test device specifically intended to overcome previous problems in achieving rapid and highly accurate detection of particular compounds in a saliva test sample. This is particularly true where the test sample must be pre-treated in order to obtain the desired rapid and accurate result. The disclosed test device is particularly suited for a saliva test sample which is very difficult to rapidly and accurately test using an immunoassay test strip.

In particular, saliva contains mucins which are a family of large, heavily glycosylated proteins which account for many of the properties of saliva. However, the mucins also act to disrupt the lateral flow necessary to achieve a rapid and accurate test result and greatly restrict both the time it takes for a sample to travel through the immunoassay strip as well as the amount of the target compound in the sample which can travel up the strip and thus be determined by the immunoassay strip.

Because of the problems caused by mucins, certain testing systems had recommended long and elaborate procedures for removing mucins prior to testing the sample. What was necessary in the art was the ability, using a single device, to pre-treat a sample such as saliva with a diluent or other reagent which is capable of breaking down the interferants in a sample, e.g., mucins in saliva, so that these interferants do not restrict the capillary flow of the sample through the test strip, which will result in a rapid test of target compounds in a more accurate manner than heretofore possible.

Accordingly, the present invention is a novel and unobvious device which essentially comprises a first chamber which contains a pre-treatment reagent, a second chamber which contains a second reagent, means for contacting a test sample with the first reagent, means for mixing the sample, the first reagent and the second reagent prior to the time the mixture is introduced to the immunoassay test strip which allows the pre-treatment reagent to dilute or denature interferants, e.g., mucins from saliva, which would otherwise obstruct and severely limit the speed and effectiveness in carrying out a rapid immunoassay on-site, such as a saliva test for an employee or prospective employee.

The present invention thus solves the specific problem of the pre-treatment of the saliva test sample in such a manner as to provide a quick and accurate reading. In the present immunoassay device, a pre-treatment first reagent from a first chamber and a second reagent from a second chamber are mixed with a sample so that the sample can be incubated and diluted and/or denatured rapidly before the test sample is then applied to the immunoassay test strip to give the accurate reading.

This improved device further gives the user the option to initiate the operative steps as may be desired to conduct a test. After a test sample of saliva has been collected, the person conducting the test depresses the buffer button to initiate the delivery of the buffer solution to the mixing chamber into which a second reagent has been placed. The test operator then delivers the test sample to the mixing chamber to mix with the buffer solution and the second reagent. The user then initiates the delivery, at his option, of the test mixture to the test strip. The flow or delivery of the test mixture to the test strip after an incubation period is controlled by the user. The flow or passage of the test sample within the testing device is under the control of the user who can selectively initiate each of; the delivery of the buffer solution, the delivery of the test sample, and the delivery of the test sample mixture to the test strip.

It will be understood that this invention is susceptible to modification in order to adapt it to different usages and conditions, and accordingly, it is desired to comprehend such modifications within this invention as may fall within the scope of the appended claims.

The invention claimed is:

1. A saliva sample testing device comprising a body member having a first cylindrical chamber for receiving a test sample and a second cylindrical chamber for receiving a first reagent, said cylindrical chambers being disposed vertically in parallel side-by-side relationship and each cylindrical chamber having a bottom end opening, means in said body member for defining a vertical passage below said first and second cylindrical chambers and having an open top end communicating with said cylindrical chambers bottom openings and further having an open bottom end, a test chamber having an immunoassay test strip therein below said vertical passage and communicating with said bottom end opening, below a mixing chamber in said vertical passage, and means in said vertical passage for defining said mixing chamber having a first position to receive a test sample and a first reagent, said mixing chamber being capable of being movable to a second position from which the mixture of the test sample and first reagent is discharged into said test chamber.

2. A saliva sample testing device as claimed in claim 1 wherein
said mixing chamber being capable of being movable to an intermediate position between said first and second positions during which said test sample and first reagent are mixed.

3. A saliva sample testing device as claimed in claim 1 wherein
said mixing chamber means comprises a cylindrical tubular member passing transversely through said vertical passage and having opposed openings therein corresponding to said vertical passage, and a rotatable cylinder in said tubular member and having a mixing chamber therein and an opening to the surface of said tubular member such that in said first position, the opening is directed upwardly to receive the test sample and first reagent and in said second position the opening is directed downwardly toward the open bottom end of the vertical passage to discharge a mixture of test sample and first reagent into said test chamber.

4. A saliva sample testing device as claimed in claim 1 and further comprising
means for defining inclined surfaces below said cylindrical chamber bottom end openings and sloping toward said vertical passage open top end.

5. A saliva sample testing device as claimed in claim 1 wherein
said test chamber is disposed horizontally.

6. A saliva sample testing device as claimed in claim 1 wherein
said test strip is supported horizontally within said test chamber.

7. A saliva sample testing device as claimed in claim 1 and further comprising means for introducing a second reagent to said mixture in said; mixing chamber.

8. A process for testing a saliva sample comprising the steps of
providing a housing having two vertically extending side-by-side positioned cylindrical chambers communicating through a vertical passage to a test chamber and there being a rotatable mixing chamber in said vertical passage,
positioning the mixing chamber in a first position,
delivering a buffer from one cylindrical chamber and delivering a test sample from the other cylindrical chamber to the mixing chamber in its first position,
rotating the mixing chamber to an intermediate position to cause mixing of the test sample and buffer agent to form a test mixture, locating the mixing chamber to a second position to discharge the test mixture into the test chamber after a predetermined period of time as lapsed to allow incubation of the test mixture.

* * * * *